United States Patent
Bougere et al.

(10) Patent No.: US 11,833,061 B2
(45) Date of Patent: Dec. 5, 2023

(54) EXPANDABLE INTERVERTEBRAL IMPLANT WITH INDEPENDENT ADJUSTMENTS

(71) Applicant: Zimmer Biomet Spine, Inc., Westminster, CO (US)

(72) Inventors: Emmanuel Bougere, Bordeaux (FR); Nicolas Bidegaimberry, Gradignan (FR); Samuel Lequette, Pessac (FR); Nicolas Roche, Saint Medard en Jalles (FR)

(73) Assignee: Zimmer Biomet Spine, Inc., Westminster, CO (US)

( * ) Notice: Subject to any disclaimer, the term of this patent is extended or adjusted under 35 U.S.C. 154(b) by 70 days.

(21) Appl. No.: 17/524,412

(22) Filed: Nov. 11, 2021

(65) Prior Publication Data
US 2022/0160515 A1 May 26, 2022

Related U.S. Application Data

(60) Provisional application No. 63/116,452, filed on Nov. 20, 2020.

(51) Int. Cl.
*A61F 2/44* (2006.01)
*A61F 2/30* (2006.01)

(52) U.S. Cl.
CPC ...... *A61F 2/447* (2013.01); *A61F 2002/3054* (2013.01); *A61F 2002/30266* (2013.01);
(Continued)

(58) Field of Classification Search
CPC ............ A61F 2/447; A61F 2/44; A61F 2/442; A61F 2/4461; A61F 2002/30266;
(Continued)

(56) References Cited

U.S. PATENT DOCUMENTS

| 6,102,950 A | * | 8/2000 | Vaccaro | A61F 2/4637 606/247 |
| 6,176,882 B1 | * | 1/2001 | Biedermann | A61F 2/447 623/17.11 |
| 9,750,618 B1 | | 9/2017 | Daffinson et al. | |

(Continued)

FOREIGN PATENT DOCUMENTS

WO   WO 2015/198335   12/2015

OTHER PUBLICATIONS

Extended European Search Report for European Patent Application No. 21209268.8, dated Apr. 25, 2022 9 pages.

*Primary Examiner* — Jessica Weiss
(74) *Attorney, Agent, or Firm* — Sheridan Ross P.C.

(57) ABSTRACT

An expandable intervertebral implant comprises an expandable cage comprising a central frame, a superior endplate, an inferior endplate, an anterior adjustment mechanism and a posterior adjustment mechanism. The central frame including an anterior (distal) threaded bore and a posterior (proximal) bore. The superior (upper) end plate movably coupled along a posterior portion of the central frame. The inferior (lower) end plate movably coupled along the posterior portion of the central frame opposite the superior end plate. The anterior adjustment mechanism including an anterior wedge coupled to an anterior screw movable within the anterior threaded bore. The posterior adjustment mechanism including a posterior wedge coupled to a posterior screw movable within the posterior bore.

20 Claims, 12 Drawing Sheets

(52) U.S. Cl.
CPC ............... *A61F 2002/30433* (2013.01); *A61F 2002/30579* (2013.01); *A61F 2002/30593* (2013.01)

(58) Field of Classification Search
CPC .... A61F 2002/30433; A61F 2002/3054; A61F 2002/30579; A61F 2002/30593
USPC .......................................... 623/17.11–17.16
See application file for complete search history.

(56) References Cited

U.S. PATENT DOCUMENTS

| | | | |
|---|---|---|---|
| 10,022,239 B1 | 7/2018 | Lentner et al. | |
| 2007/0270968 A1* | 11/2007 | Baynham | A61F 2/447 |
| | | | 623/17.11 |
| 2011/0172774 A1* | 7/2011 | Varela | A61F 2/447 |
| | | | 623/17.16 |
| 2012/0029636 A1* | 2/2012 | Ragab | A61F 2/447 |
| | | | 623/17.11 |
| 2013/0158663 A1* | 6/2013 | Miller | A61F 2/447 |
| | | | 623/17.16 |
| 2013/0158664 A1* | 6/2013 | Palmatier | A61F 2/4425 |
| | | | 623/17.16 |
| 2013/0211525 A1* | 8/2013 | McLuen | A61F 2/4455 |
| | | | 623/17.16 |
| 2015/0148908 A1 | 5/2015 | Marino et al. | |
| 2016/0166396 A1 | 6/2016 | Mcclintock | |
| 2016/0354212 A1 | 12/2016 | Baynham | |
| 2018/0000606 A1* | 1/2018 | Hessler | A61F 2/30771 |
| 2018/0116816 A1 | 5/2018 | Weiman et al. | |
| 2019/0254836 A1 | 8/2019 | Cowan et al. | |
| 2020/0129307 A1 | 4/2020 | Hunziker et al. | |
| 2022/0133496 A1* | 5/2022 | Dewey | A61F 2/4611 |
| | | | 623/17.16 |
| 2022/0175547 A1* | 6/2022 | Fresneau | A61F 2/447 |

\* cited by examiner

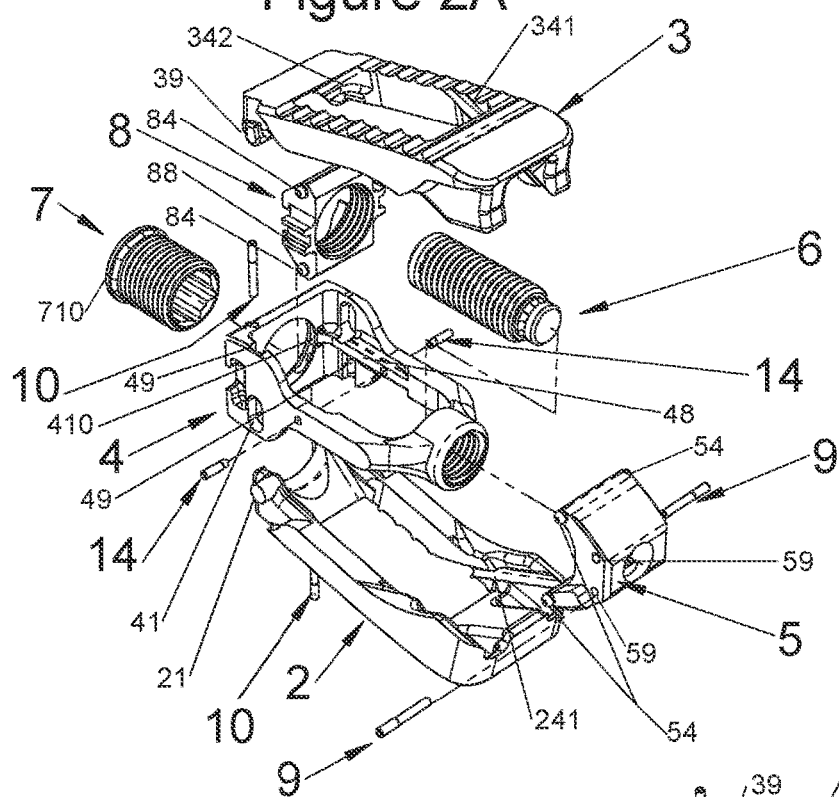
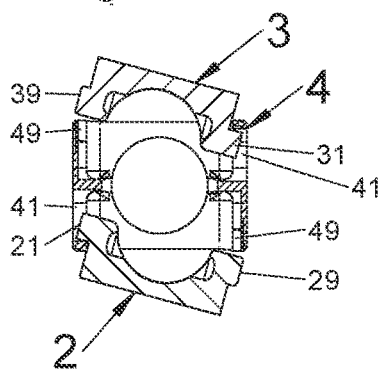
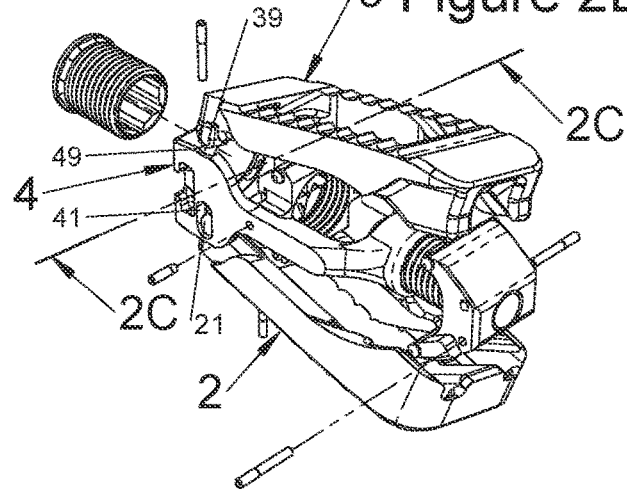
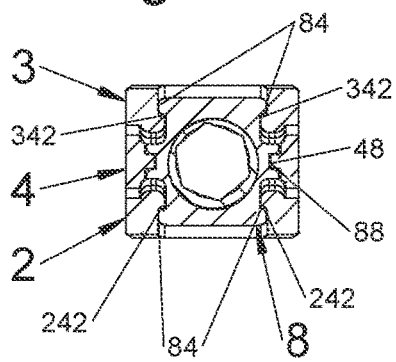
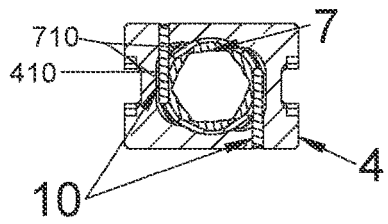
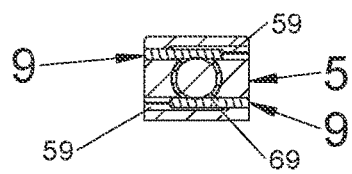

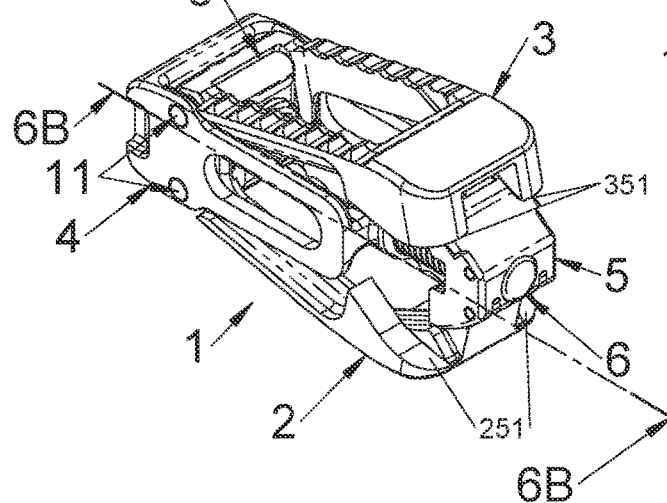
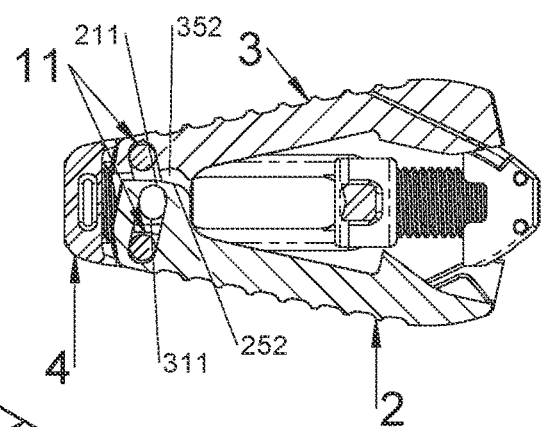
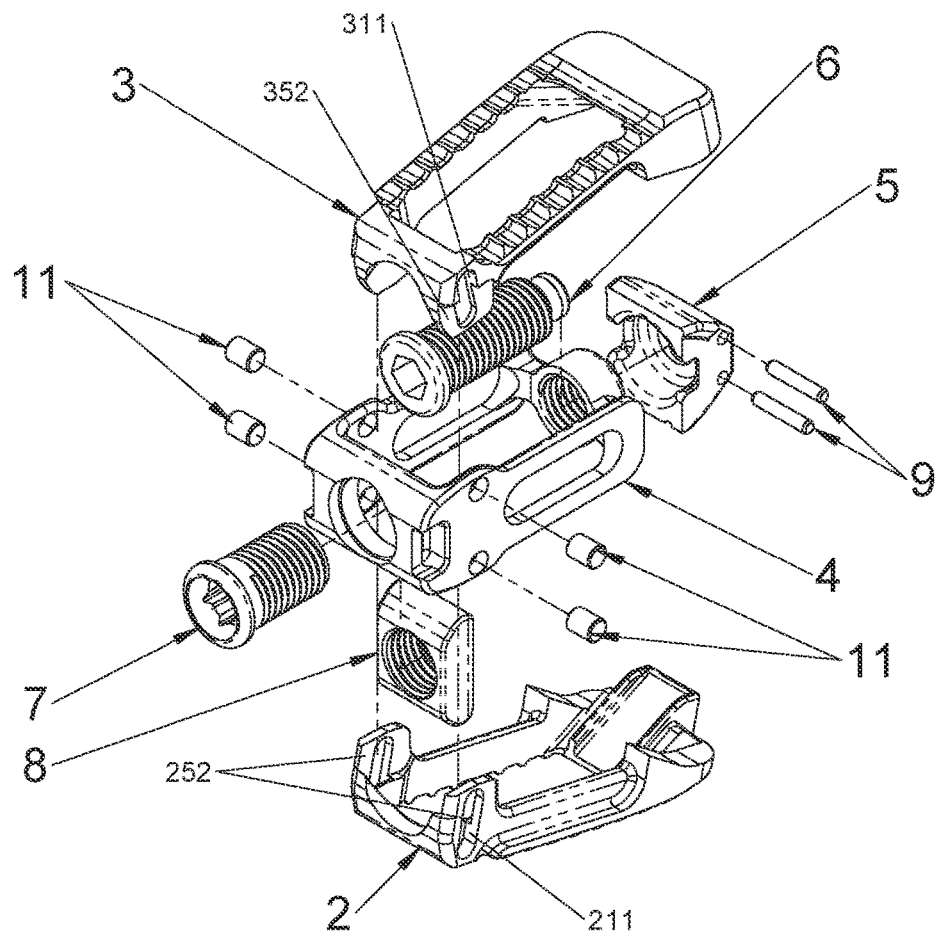

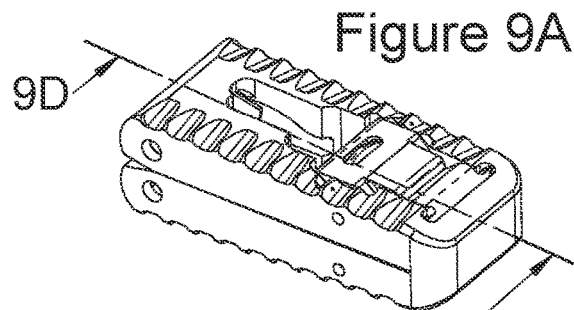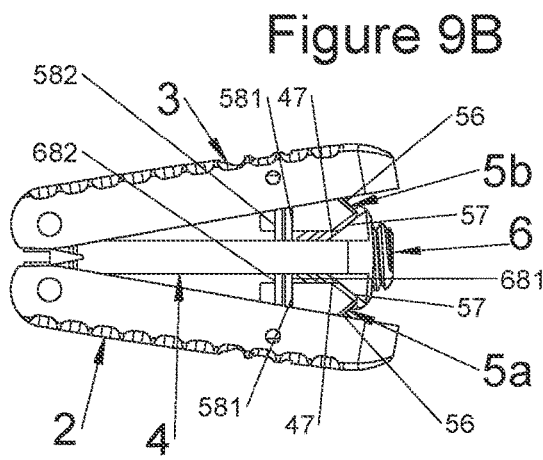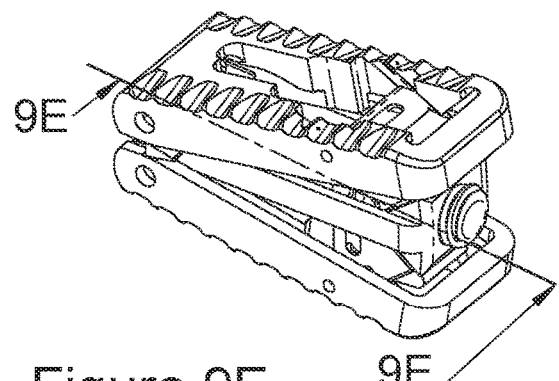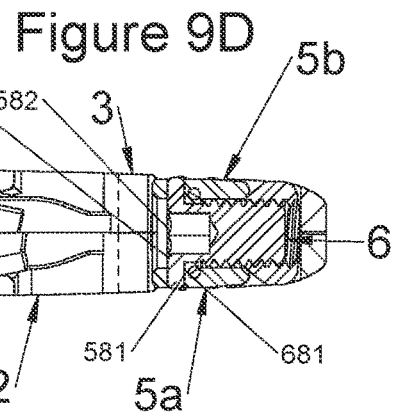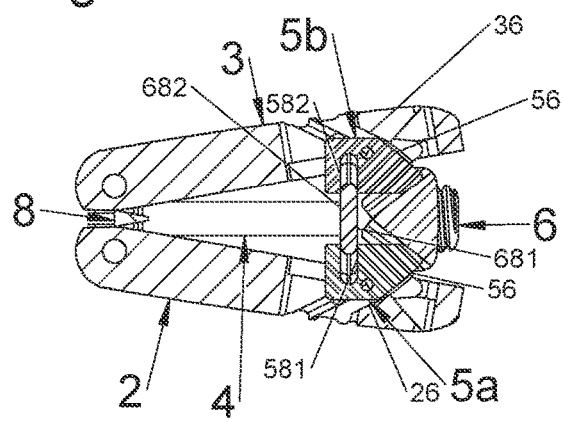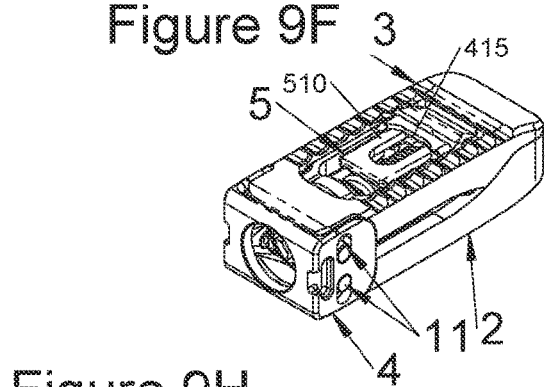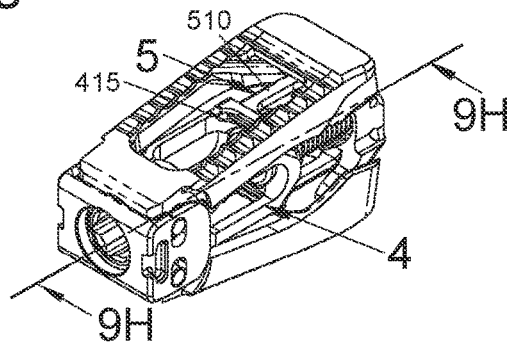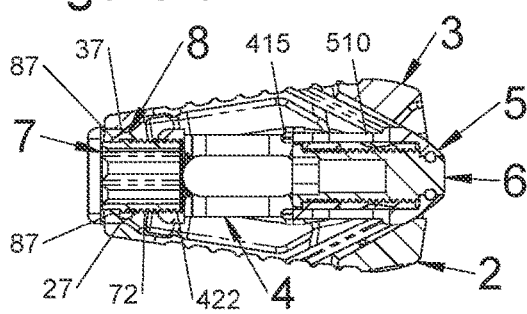

EXPANDABLE INTERVERTEBRAL IMPLANT WITH INDEPENDENT ADJUSTMENTS

CLAIM OF PRIORITY

This application claims the benefit of U.S. Provisional Patent Application Ser. No. 63/116,452, filed on Nov. 20, 2020, the benefit of priority of which is claimed hereby, and which is incorporated by reference herein in its entirety.

TECHNICAL FIELD

This document pertains generally, but not by way of limitation, to implants for positioning between adjacent bones, such as can be used in spinal correction procedures. More specifically, but not by way of limitation, the present application relates to intervertebral implants that are expandable.

BACKGROUND

A spinal column can require correction of spinal deformities and abnormalities resulting from trauma or degenerative issues. Various methods of correcting issues with the spinal column can include fusing adjacent vertebrae together with a spacer and/or a rod system to immobilize the degenerated portion of the spine. Such procedures can be beneficial in patients having diseased or degenerated disc material between the vertebrae. For example, intervertebral implants can be positioned between adjacent vertebrae to fuse the vertebrae together, after disk material located therebetween is removed. In order to facilitate insertion between the adjacent vertebrae, the implants can be configured to expand. As such, the implant can be collapsed to have a smaller height for insertion and after being positioned into the target anatomy can be expanded to a taller height to provide the desired spacing. It can, however, be difficult to expand the implant to the desired level due to, for example, resistance from the anatomy.

Examples of expandable intervertebral spacer implants are described in Pub. No. US 2015/0148908 to Marino et al.; Pub. No. US 2016/0354212 to Baynham; Pub. No. US 2020/0129307 to Hunziker et al.; and Pub. No. US 2016/0166396 to McClintock et al.

OVERVIEW

The present inventors have recognized, among other things, that a problem to be solved can include the lack of variability in lordotic expansion for traditional expandable intervertebral spacers. In particular, the present inventors have recognized that many typical expandable implants utilize only a single mechanism to expand the implant. As such, each of these implants typically include tradeoffs between providing bone support, expansion height, mechanical advantage, and lordotic expansion angles. For example, most expandable intervertebral implants utilize a single actuation mechanism that limits the variability in achievable angles of lordotic expansion (e.g., greater height expansion for distal (or anterior) side of implant versus proximal (or posterior) side). The current inventors recognize that providing a surgeon with the ability to adjust the amount of expansion as well as the amount of lordotic angle provides greater intraoperative flexibility to achieve desire spinal correction.

The present subject matter can help provide a solution to these problems, such as by providing an interbody implant that is configured to expand using two different expansion mechanisms. The two different expansion mechanisms (anterior and posterior) can be configured to be deployed independently through separate adjustment mechanisms. For example, a first (anterior) expansion mechanism adjusts the expansion height of the anterior portion of the implant, while a second (posterior) expansion mechanism adjusts the posterior expansion height. In examples, the expansion mechanisms can be configured to work cooperatively, e.g., at the same time, and then exclusively, e.g., one at a time. In other examples, the expansion mechanisms can be configured to operate sequentially, e.g., one and then the other. In an example, the expansion (or adjustment) mechanisms operate independently, so it is a function of the implant instrument to allow for concurrent and also independent operation of the expansion mechanisms.

In an example, an intervertebral implant can comprise a first cage (end plate), a second cage (end plate), a central frame, a distal (anterior) wedge, a distal (anterior) adjustment mechanism, a proximal (posterior) wedge, and a proximal (posterior) adjustment mechanism. In this example, the adjustment mechanisms include a threaded screw rotationally coupled to the central frame. In some examples, the distal adjustment mechanism can include a distal screw threadably engaged with a thread bore in the central frame. In certain examples, the proximal screw can be free to rotate with a proximal bore in the central frame, but is translationally fixed relative to the frame.

In another example, a method of inserting an intervertebral implant can comprise inserting the intervertebral implant into anatomy of a patient, the intervertebral implant comprising a first (superior) end plate and a second (inferior) end plate coupled to opposing sides of a central frame housing the first (distal) and second (proximal) adjustment mechanisms. The method can continue with expansion of the implant by operating the first expansion mechanism to expand the distal height of the implant and by operating the second adjustment mechanism to expand the proximal height of the implant.

Additional examples of variations in the adjustment mechanisms, end plates, and central frame are discussed in detail below.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

FIG. 2A is an exploded view of the expandable interbody implant with independently adjustable expansion mechanisms, according to an example embodiment.

FIGS. 2B-2C are various assembly drawings of an expandable interbody implant with independently adjustable expansion mechanisms, according to an example embodiment.

FIG. 2D is a cross-sectional view illustrating end plate retention structures built into expansion wedges, operable within any of the example embodiments.

FIGS. 2E-2F are cross-sectional drawings of expansion mechanism retention pins, operable within any of the example embodiments.

FIGS. 6A-6C are various drawings illustrating an alternative proximal end plate configuration operable with any of the example embodiments.

FIGS. 9A-9E are various drawings illustrating a double wedge distal expansion mechanism operative within any of the example embodiments.

FIGS. 9F-9H are various drawings illustrating an example distal expansion mechanism operable within any of the example embodiments.

Figure 1A:
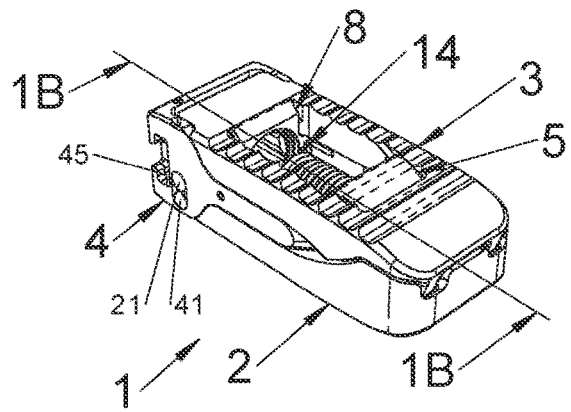
FIGS. 1A-1B are perspective and cross-sectional views of an expandable interbody implant with independently adjustable expansion mechanisms in a closed state, according to an example embodiment.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document. As eluded to in the drawing descriptions and further detailed below, many of the illustrated example structures can be utilized across different embodiments, as would be understood by a person of ordinary skill in the art.

DETAILED DESCRIPTION

The expandable intervertebral implant discussed in detail below includes differentiated proximal (posterior) and distal (anterior) expansion with wedges actuated by screw-based adjustment mechanisms. The embodiments discussed below include a central frame, upper (superior) and lower (inferior) end plates, and proximal and distal adjustment mechanisms. The proximal and distal adjustment mechanisms involve threaded screws coupled in some manner to the central frame. In some examples, the distal screw is threadably engaged with a threaded bore in a distal portion of the central frame. In certain examples, the distal screw includes two threaded portions one threadably engaged with the threaded bore in the central frame and the second threadably engaged with the distal wedge. In these examples, articulation of the distal screw results in linear translation of the distal wedge, which enables height adjustment of the distal ends of the end plates. The height adjustment is enabled through interaction between the distal wedge and ramped surfaces on the interior sides of the end plates (e.g., on the inferior side of the superior end plate and on the superior side of the inferior end plate). The screw-based adjustment mechanisms allow for infinitely variable adjustment of proximal and distal height within the overall adjustment range. The overall adjustment range is dictated by the wedge size and ramped surfaces on the end plates. In some examples, distal expansion is extended through crossed (interleaved) arrangement between ramped surfaces of the opposing end plates, which allows the expended height to exceed the height of the wedge alone.

In some examples, the proximal adjustment screw is cylindrical to allow passage of the adjustment instrument to articulate the distal adjustment screw. The cylindrical structure of the proximal adjustment screw also enables post-packing of bone graft materials into the central frame and end plates. Both the central frame and the end plate can include large lateral and vertical openings to enable passage of bone graft material into the adjacent disc space.

The following discussion of the drawings provides detailed explanation of the various different expansion mechanisms, end plate structures, central frame structures, and assembly techniques for the expandable interbody implants. A person of ordinary skill in the art will understand that many of the different structures described below can be combined in manner not specifically discussed, but within the understanding of the present inventors.

FIGS. 1A-1F illustrate an example expandable interbody implant across three distinct states of expansion-closed (collapsed), distal (anterior) expansion, and distal and proximal (posterior) expansion. In this example, the expandable interbody implant 1 ("the implant 1") includes a lower (inferior) endplate 2, an upper (superior) endplate 3, a central frame 4, a distal (anterior) wedge 5, a distal (anterior) screw 6, a proximal (posterior) screw 7, and a proximal (posterior) wedge 8. Additional components of this example of the implant 1 as discussed below in reference to the different state of expansion figures.

Figure 1B:
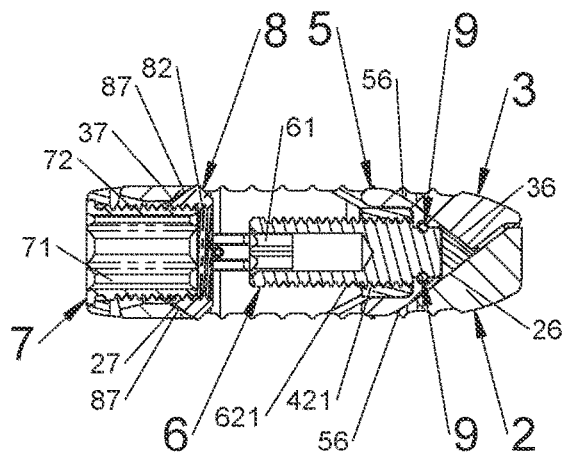

FIGS. 1A-1B are perspective and cross-sectional views of implant 1 with the independently adjustable expansion mechanisms in a closed state, according to an example embodiment. In this example, both the proximal and distal expansion mechanism are in a closed state (or implant state). The implant 1 is designed for implantation in a closed or collapsed state to minimize soft tissue disruption and ease implantation. In this example, the distal expansion mechanism includes the distal screw 6 coupled to the distal wedge 5 with assembly pins 9. In some embodiments, assembly pins 9 are elastic pins that allow the distal screw 6 to rotate relative to the distal wedge 5, but prevent relative translation between the distal screw 6 and the distal wedge 5. The implant holder interface 45 on the proximal end of the central frame 4 is also illustrated. The implant holder interface 45 provides a t-shape slot for engaging the implant instrument allows for manipulation of the implant during the implant procedure.

FIG. 1A also illustrates a lower endplate pin 21 within an endplate guide slot 41 in the central frame 4. The lower endplate pin 21 retains the lower endplate 2 within the guide slot 41, which allows for vertical expansion of the lower endplate 2 relative to the central frame 4.

FIG. 1B is a cross-sectional illustrating depicting various internal structures of the example implant 1. Starting with the distal expansion mechanism, FIG. 1B illustrates the distal wedge 5 including opposing angled surfaces 56 that engage with a distal lower angled surface 26 on the superior surface of the lower endplate 2 and a distal upper angled surface 36 on the inferior surface of the upper endplate 3. Interaction of these angled surfaces enables expansion of the distal end of the implant 1. The angulation of these angled surfaces also dictates the amount of expansion and expansion force the implant 1 can exert and adjacent vertebral bodies during implantation. The distal expansion mechanism further includes the distal screw 6 with threads 621 engaging a threaded portion 421 of the central frame 4. The distal screw 6 also includes a drive socket 61 that can receive an expansion driver portion of an implant instrument. Rotation of the expansion driver when engaged with the drive socket 61 results in linear translation of the distal wedge 5, which in turn causes vertical separation of the distal ends of the lower endplate 2 and the upper endplate 3.

In this example, the proximal expansion mechanism includes proximal wedge 8 with opposing angled surfaces 87 that engage with a lower angled surface 27 extending from an superior surface of the lower endplate 2 and an upper angled surface 37 extending from an inferior surface of the upper endplate 3 (elements 27 and 37 also referred to as endplate angled surfaces). The proximal wedge 8 also includes a threaded bore 82 that engages with threads 72 on the proximal screw 7. In this example, the proximal screw 7 is translationally fixed relative to the central frame 4. The proximal screw 7 further includes a drive socket 71 to receive a proximal expansion driver portion of an implant instrument.

Figure 1C:
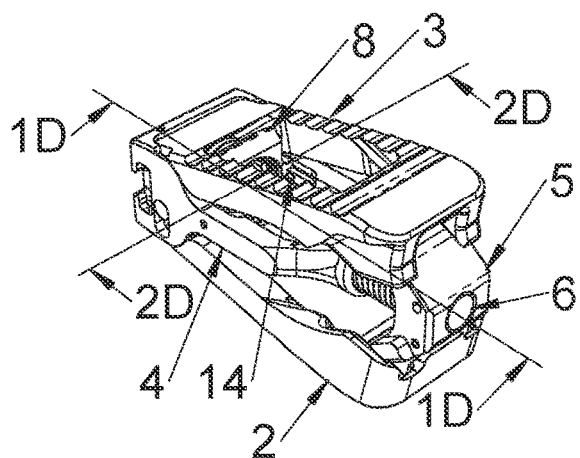
FIGS. 1C-1D are perspective and cross-sectional views of the expandable interbody implant with independently adjustable expansion mechanisms with distal expansion only, according to an example embodiment.
Figure 1D:
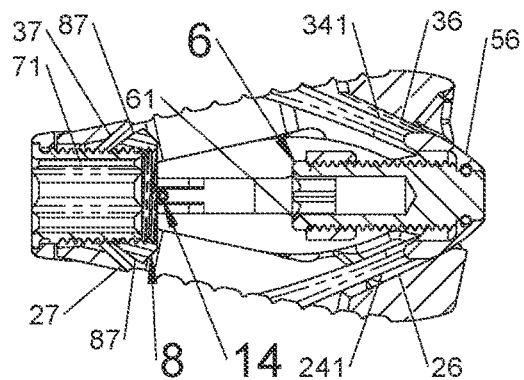

FIGS. 1C-1D are perspective and cross-sectional views of the implant 1 with independently adjustable expansion mechanisms with distal expansion only, according to an example embodiment. In this example, the distal expansion mechanism is fully expanded separating the distal ends of the lower endplate 2 and the upper endplate 3 to the fullest extent of the design. As shown, the distal wedge 5 is advanced distally between the lower endplate 2 and the upper endplate 3 engaging the angled surfaces 26, 36 on the respective endplates. The distal screw 6 has also translated distally within the distal threaded bore (e.g., threaded portion 421) in the central frame 4. FIG. 1D illustrates overexpansion slots 241 and 341 on the lower endplate 2 and upper endplate 3 respectively. The overexpansion grooves 241, 341 operate to prevent the distal wedge 5 from pushing to far distally and dislodging from the endplates. As illustrated below FIG. 2A, the distal wedge 5 includes overexpansion pegs 54 extending from each outer corner of the wedge.

Figure 1E:
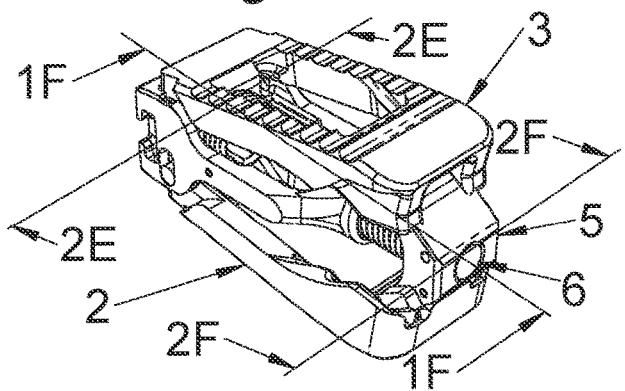
FIGS. 1E-1F are perspective and cross-sectional views of the expandable interbody implant with independently adjustable expansion mechanisms with distal and proximal expansion, according to an example embodiment.
Figure 1F:
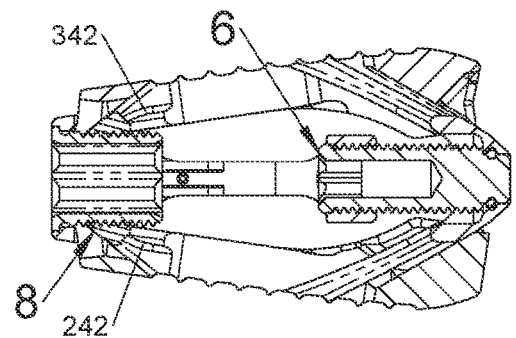

FIGS. 1E-1F are perspective and cross-sectional views of the implant 1 with independently adjustable expansion mechanisms with distal and proximal expansion, according to an example embodiment. In this example, the proximal expansion mechanism (e.g., proximal screw 7 and proximal wedge 8) are engaged to expand the proximal ends of the lower endplate 2 and upper endplate 3 to the furthest extent of the design. Similar to the distal expansion mechanism, the proximal wedge 8 is captured within proximal overexpansion grooves 242 and 342 in the lower endplate 2 and upper endplate 3 respectively.

FIG. 2A is an exploded view of the expandable interbody implant 1 with independently adjustable expansion mechanisms, according to an example embodiment. In this example, all the individual components of the implant 1 are illustrated. In this example, the lower endplate 2 includes a lower endplate pin 21 that extends through the guide slot 41 in the central frame 4. The distal overexpansion groove 241 of the lower endplate 2 is also shown. The upper endplate 3 also includes a distal overexpansion groove 341 as well as a proximal overexpansion groove 342. The upper endplate 3 further includes an upper endplate pin 39 that engages with vertical guide groove 49 to restrict movement of the proximal end of upper endplate in a vertical direction.

In this example, the central frame 4 includes proximal screw assembly pin(s) 10, proximal wedge locking pin(s) 14, guide slot 41, proximal wedge horizonal guide slot 48, and vertical guide groove 49. The proximal screw assembly pin(s) 10 extend vertically into a periphery of the proximal screw bore to capture the proximal screw 7 within the central frame 4. In this example, the proximal screw assembly pin(s) 10 retain the proximal screw 7 in translation relative to the central frame 4, while allowing the proximal screw 7 to rotate. In this example, there are two proximal screw assembly pins 10, one illustrated above the central frame 4 and the other below the central frame 4. The proximal screw assembly pins 10 are received through apertures in opposing sides of the central frame 4 into pin grooves 410 that are partially exposed to the bore that the proximal screw extends into in the proximal portion of the central frame 4. Proximal screw assembly pins 10 can flex within the pin grooves 410 to allow rotation of the proximal screw 7. The proximal wedge locking pins 14 extend through opposing lateral sides of the central frame 4 to capture the proximal wedge 8. The locking pins 14 engage a guidance groove 88 on the lateral sides of the proximal wedge 8. In this example, the guidance groove 88 on the proximal wedge 8 is also adapted to engage a corresponding proximal wedge horizonal guide slot 48 milled (or otherwise formed) in the lateral sides of the central frame 4.

In this example, the distal wedge 5 includes structures such as overexpansion pegs 54 and pin holes 59. The pin holes 59 receive assembly pins 9 to capture the distal screw 6 within the distal wedge 5. The assembly pins 9 can be elastic pins that allow for the distal screw 6 to rotation within the distal wedge 5, but prevent relative translation between the distal screw 6 and the distal wedge 5. The proximal wedge 8 includes overexpansion pegs 84 and guidance groove 88, as discussed above. Finally, the proximal screw 7 includes flats 710, which operate in coordination with proximal screw assembly pins 10 to lock the proximal screw 7 into the central frame 4.

FIGS. 2B-2C are various assembly drawings of the implant 1 with independently adjustable expansion mechanisms, according to an example embodiment. In this example, the implant 1 is assembly by tilting the endplates (lower endplate 2 and upper endplate 3) into the central frame 4. As shown in FIG. 2C, the lower endplate 2 is angled to insert the lower endplate pin 21 into guide slot 41 and then the lower endplate pin 29 is slid into vertical guide groove 49. The upper endplate 3 is assembled in a similar fashion. The upper endplate pin 31 is tilted into an opposing guide slot 41 and upper endplate pin 39 is slid into another vertical guide groove 49.

FIG. 2D is a cross-sectional view illustrating end plate retention structures built into expansion wedges, such as the proximal wedge 8. In this example, the proximal wedge 8 includes overexpansion pegs 84 extending from all four outer corners. The overexpansion pegs 84 extend into proximal overexpansion grooves 242 on the lower endplate 2, and proximal overexpansion grooves 342 on the upper endplate 3. The cross-sectional view also illustrates the interaction between proximal wedge horizonal guide slot 48 and guidance groove 88.

FIGS. 2E-2F are cross-sectional drawings of expansion mechanism retention pins, operable within any of the example embodiments. In these examples, assembly pins 9 and 10 are illustrated. FIG. 2E is a cross-sectional view illustrating how proximal screw assembly pins 10 extend vertically into a proximal portion of the central frame 4 to capture proximal screw 7 vie interaction with flats 710. FIG. 2F is a cross-sectional view illustrating how distal wedge assembly pins 9 capture the distal end of the distal screw 6 within the distal wedge 5. The distal wedge 5 includes pin holes 59 to receive assembly pins 9, which engage flats 69 on the distal end of the distal screw 6.

Figure 3A:
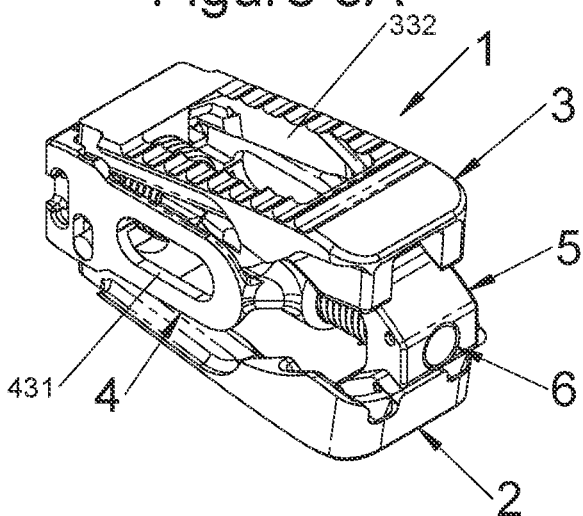
FIGS. 3A-3F are various drawings of expandable interbody implants illustrating bone graft openings within structures of implants with independently adjustable expansion mechanisms, illustrated structures are operable within any of the example embodiments.
Figure 3B:
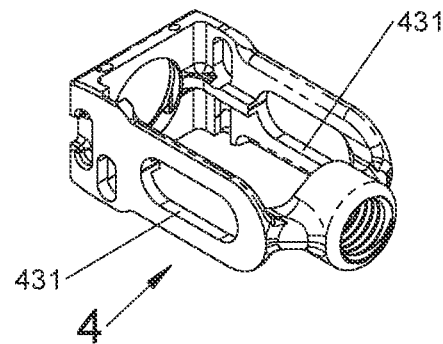
Figure 3C:
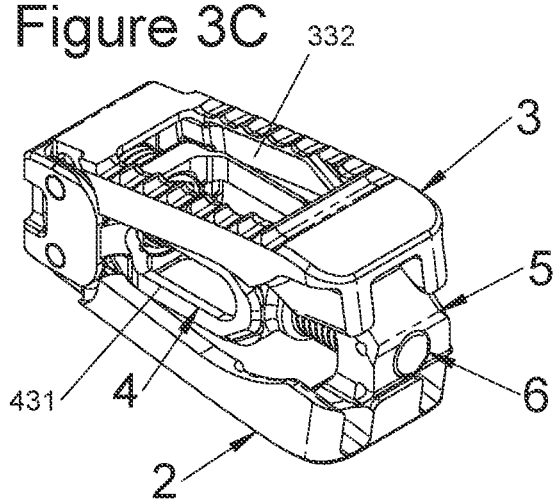
Figure 3D:
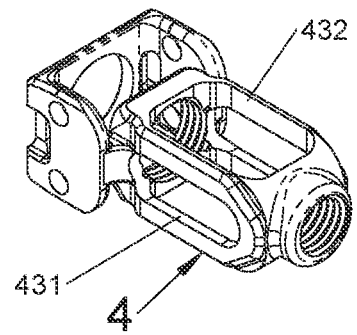
Figure 3E:
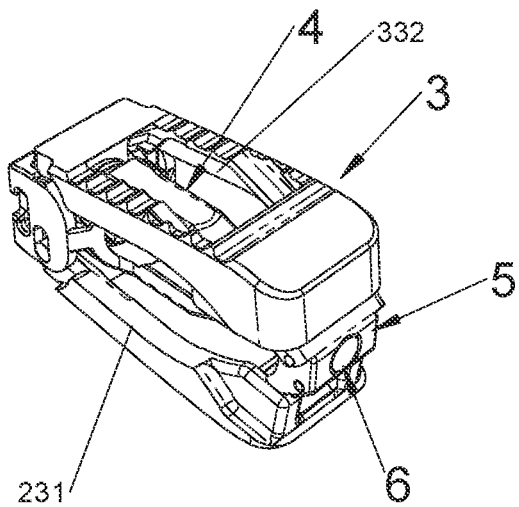
Figure 3F:
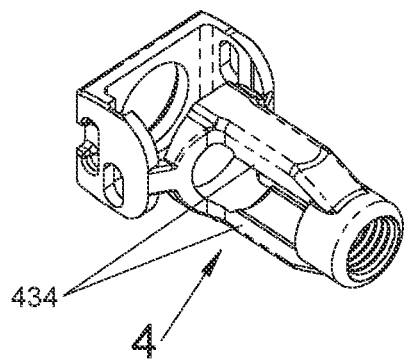

FIGS. 3A-3F are various drawings of three different configurations for implant 1 that all illustrating bone graft openings, illustrated structures are operable within any of the example embodiments. Each pair of drawings illustrates a full implant and central frame combination. FIGS. 3A-3B illustrate an external central frame where the majority of the body of the central frame 4 surrounds the endplates and expansion mechanisms. FIGS. 3C-3D illustrate a first internal frame design where the majority of the central frame 4 is within the endplates. In this example, the proximal end of the central frame 4 surrounds the proximal end of the endplates (e.g., lower endplate 2 and upper endplate 3). FIGS. 3E-3F illustrate a second internal frame design where the majority of the central frame 4 is internal to the endplates (when the implant is assembled). The central frame 4 illustrated in FIG. 3F includes a superior/inferior support structure 434 instead of the vertical bone graft openings 432 shown in FIG. 3D. These examples also illustrate various positions for lateral bone graft openings 231, 431 and vertical bone graft openings 332, 432.

Figure 4A:
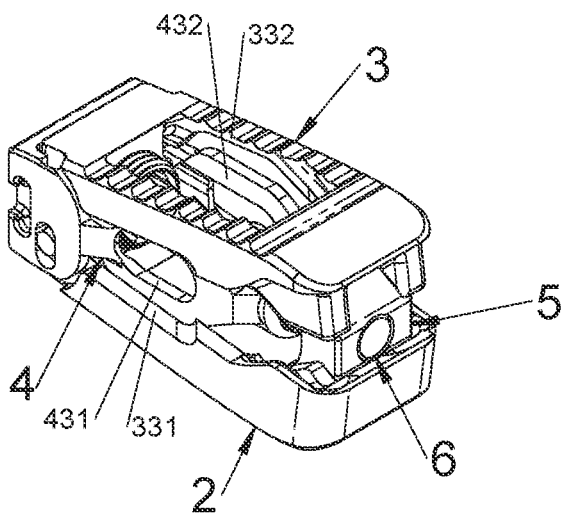
FIGS. 4A-4B are perspective drawings of an expandable interbody implant using an outer-inner central frame structure, according to an example embodiment.
Figure 4B:
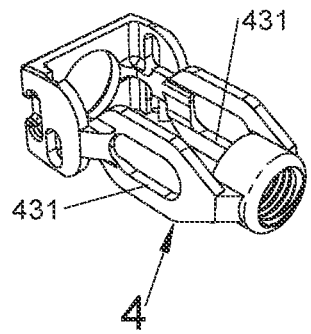

FIGS. 4A-4B are perspective drawings of implant 1 using an outer-inner central frame structure, according to an example embodiment. This example illustrates another example of an outer-inner frame structure (primarily internal central frame 4), similar to those discussed above in reference to FIGS. 3A-3F. The implant 1 in these figures also includes lateral bone graft openings 331, 231 and vertical bone graft openings 332, 432.

Figure 4C:
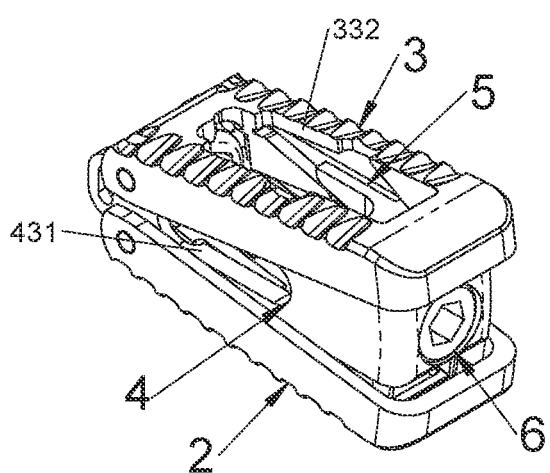
FIGS. 4C-4D are perspective drawings of an expandable interbody implant using an inner central frame structure, according to an example embodiment.
Figure 4D:
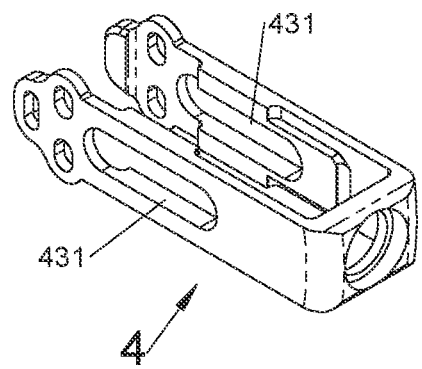

FIGS. 4C-4D are perspective drawings of implant 1 using an inner central frame structure, according to an example embodiment. In this example, the central frame 4 is completely internal to the endplates, as shown in FIG. 4C. This example also includes lateral bone graft openings 431 and vertical bone graft openings 332.

Figure 4E:
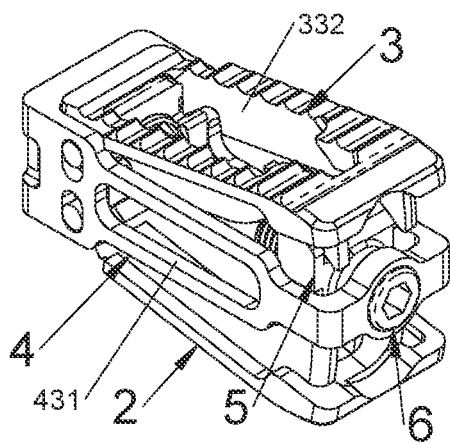
FIGS. 4E-4F are perspective drawings of an expandable interbody implant using an outer central frame structure, according to an example embodiment.
Figure 4F:
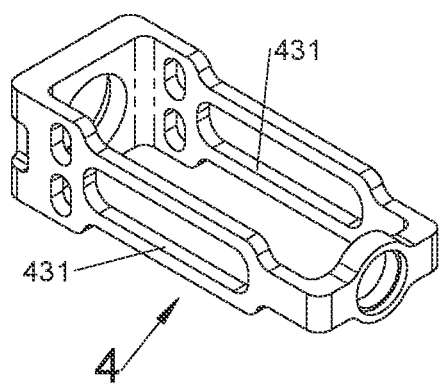

FIGS. 4E-4F are perspective drawings of implant 1 using an outer central frame structure, according to an example embodiment. In this example, the central frame 4 is completely external to the endplates as shown in FIG. 4E. This example also includes lateral bone graft openings 431 and vertical bone graft openings 332.

Figure 5A:
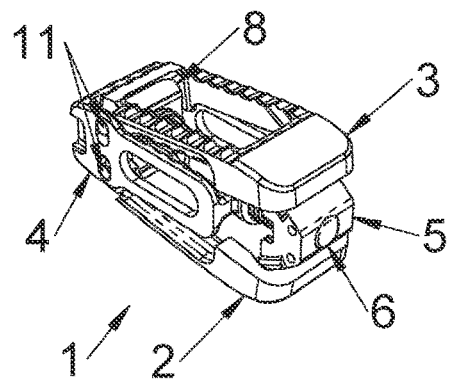
FIGS. 5A-5K are various drawings illustrating different distal end plate configurations operable with any of the example embodiments.
Figure 5B:
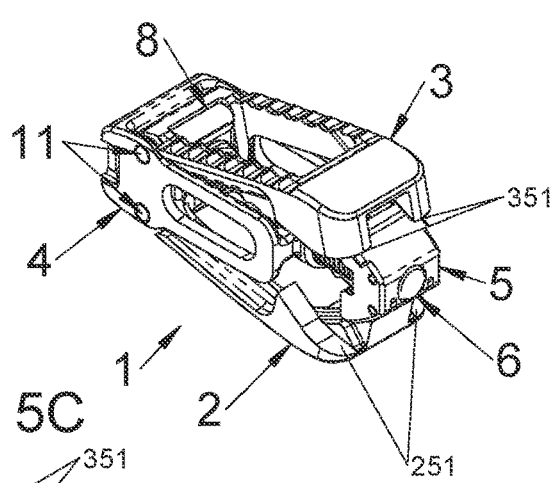
Figure 5D:
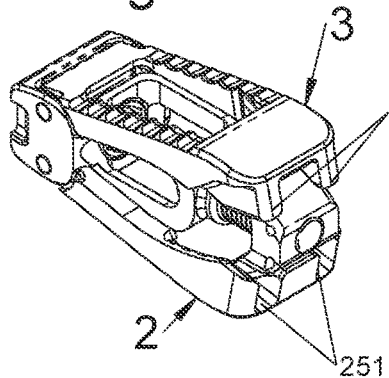
Figure 5C:
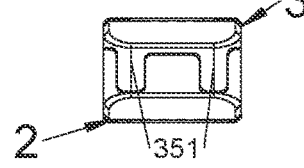
Figure 5F:
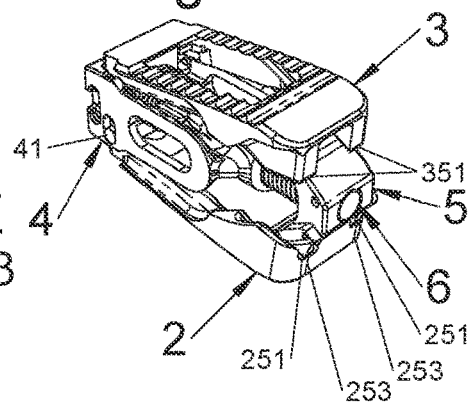
Figure 5E:
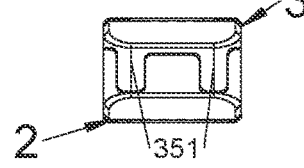
Figure 5H:
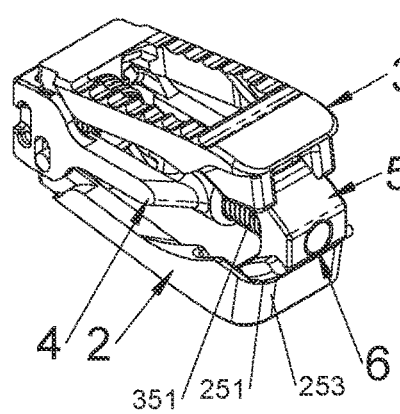
Figure 5I:
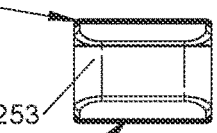
Figure 5G:
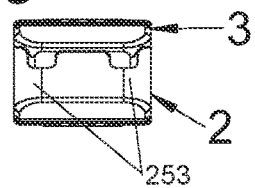
Figure 5J:
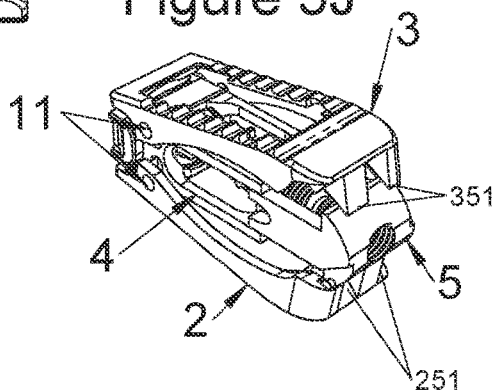
Figure 5K:
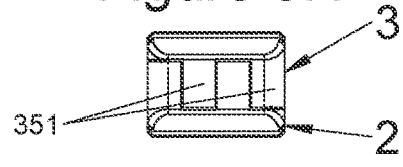

FIGS. 5A-5K are various drawings illustrating different configurations for the distal end portion of the endplates, which are operable with any of the example embodiments. FIG. 5A illustrates an implant 1 with a lower endplate 2 and an upper endplate 3 that have no crossing or interleaved portion. FIG. 5B illustrates an implant 1 with a lower endplate 2 and an upper endplate 3 with crossed portions 251, 351. In this example, the lower endplate 2 includes a center crossed portion 251 that can be interleaved with crossed portions 351 extending inferiorly from the upper endplate 3. The crossed portions 251, 351 are shown in a closed (collapsed) state in FIG. 5C. FIG. 5D illustrates an alternative configuration for crossed portions 251, 351 where the crossed portions 251 form two recesses in the lower endplate 2 and the crossed portions 351 form protrusions extending inferiorly from the upper endplate 3. FIG. 5E illustrates the crossed portions 251, 351 from FIG. 5D in a closed state. In all of these examples, the cross portions 251, 351 form a part of ramped surfaces on the endplates or are immediately adjacent to ramped portions. The crossed portions 251, 351 allow for the ramped surfaces to be larger on each endplate and enable more vertical expansion of the distal portion of the endplates. FIGS. 5F-5K illustrate additional example configurations for the crossed portions 251, 351.

FIGS. 6A-6C are various drawings illustrating an alternative proximal end plate configuration operable with any of the example embodiments. In this example, the proximal portion of each endplate (e.g., lower endplate 2 and upper endplate 3) also includes crossed portions, such as crossed portions 252, 352. In this example, the lower endplate 2 includes distal crossed portion 251 and proximal crossed portion 252, which enable the endplates to collapse into a smaller form factor in the closed state. The upper endplate includes distal crossed portion 351 and proximal crossed portion 352.

The implant 1 in this example uses an external central frame, central frame 4 and the endplates are secured on the proximal end with proximal endplate assembly pins 11. In this example, the proximal endplate assembly pins 11 extend through a proximal portion of central frame 4 to engage endplate expansion guides 211, 311. In this example, the proximal endplate assembly pins 11 are press fit into corresponding holes in the central frame 4. As illustrated in FIG. 6C, the proximal endplate assembly pins 11 engage the endplate expansion guides 211, 311, which are located at least partially within the crossed portions 252, 352 respectively.

FIGS. 7A-7E are various drawings illustrating an example distal screw arrangement operable within any of the example embodiments. In this example, the distal expansion mechanism (e.g., distal wedge 5 and distal screw 6) includes a first threaded portion 621 and a second threaded portion 622. The first threaded portion 621 engages with threaded portion 421 on the central frame 4, while the second threaded portion 622 engages with threaded portion 522 on the distal wedge 5. The two different threaded portions doubles the speed of expansion as rotation of the distal screw 6 translates the distal screw 6 with respect to the central frame 4 (via threaded portions 421 and 621) and also translates the distal wedge with respect to the distal screw (via threaded portions 522 and 622). A comparison of FIG. 7B (closed state) and FIG. 7E (expanded state) demonstrates the linear movement of both the distal wedge 5 and the distal screw 6.

Figure 7A:
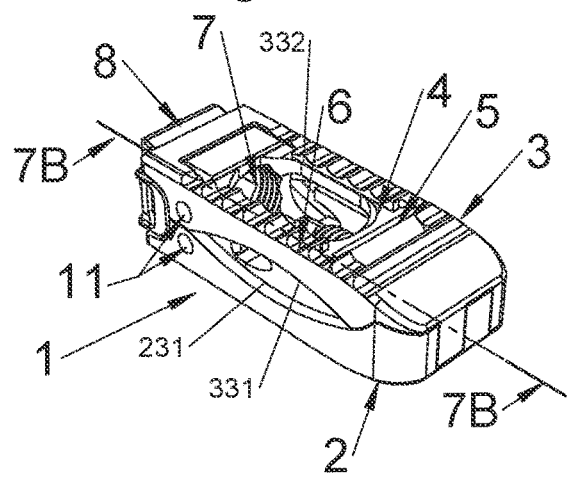
FIGS. 7A-7E are various drawings illustrating an example distal screw arrangement operable within any of the example embodiments.
Figure 7B:
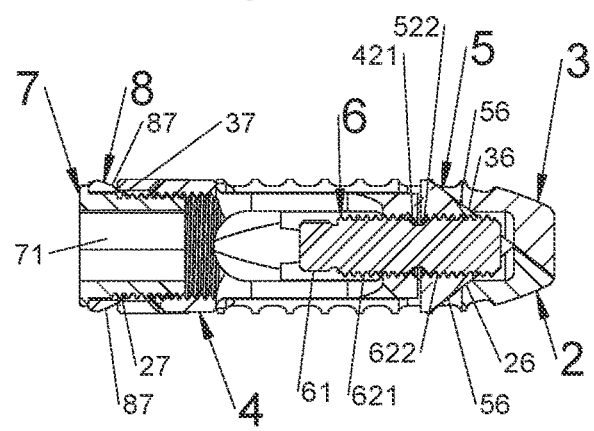
Figure 7C:
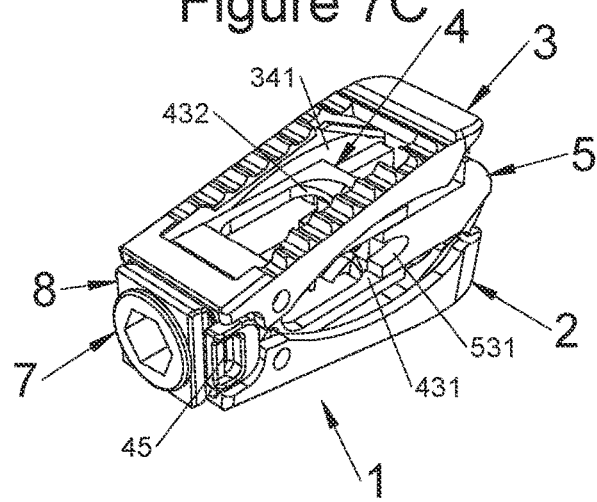
Figure 7D:
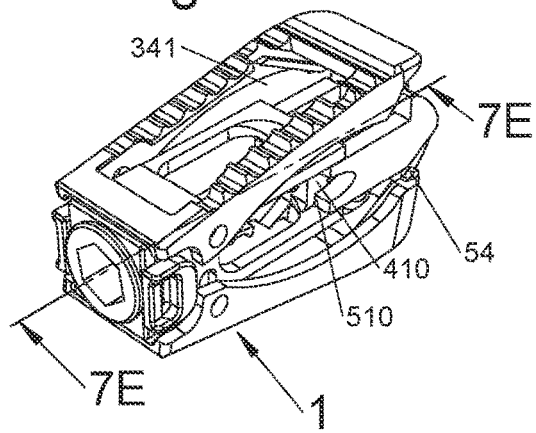
Figure 7E:
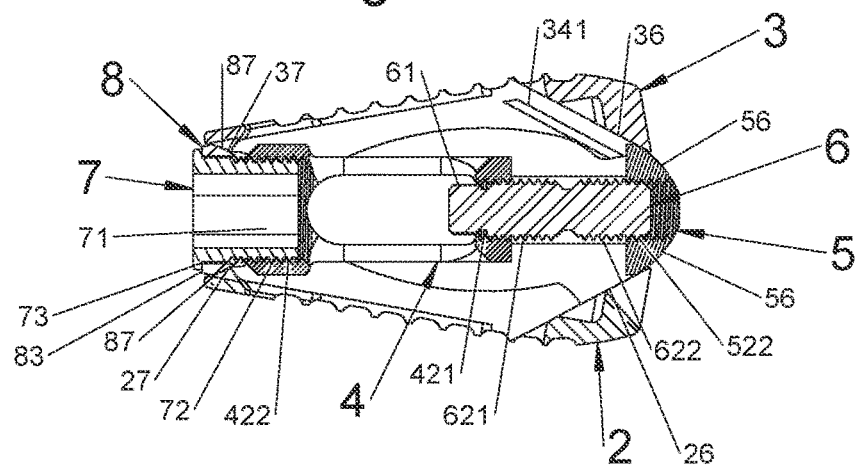

FIGS. 7B and 7E also illustrate an alternative arrangement for the proximal expansion mechanism (e.g., proximal screw 7 and proximal wedge 8). In this example, the proximal wedge 8 includes angled surfaces 87 that interact with endplate angled surfaces 27, 37 on the lower endplate 2 and upper endplate 3 respectively. The proximal wedge 8 is translationally fixed to the proximal end of the proximal screw 7, and the proximal screw 7 translates upon rotation relative to the central frame 4 via threaded portions 72, 422. The proximal wedge 8 engages the proximal screw 7 at planar edges 73, 83. Planar edge 73 is formed on the proximal end of the proximal screw 7 and abuts planar edge 83 formed by the proximal end of the proximal wedge 8.

Figure 8A:
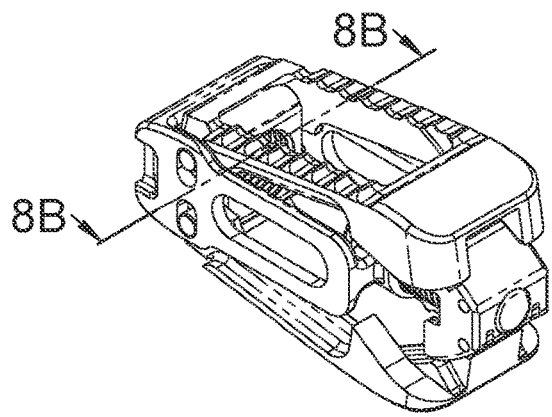
FIGS. 8A-8C are various drawings illustrating an example proximal expansion mechanism operable within any of the example embodiments.
Figure 8B:
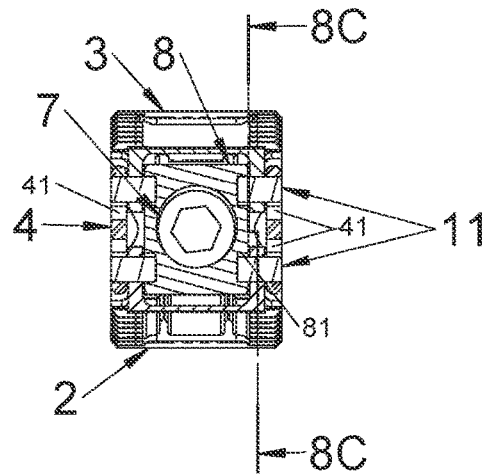
Figure 8C:
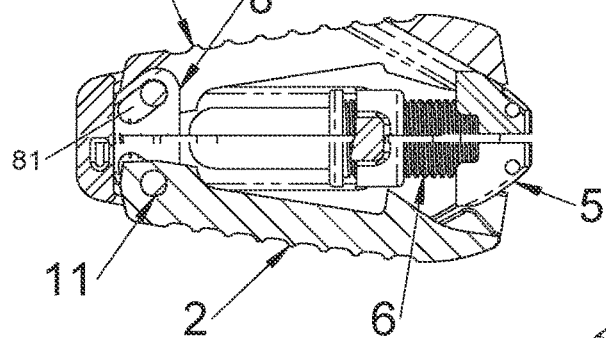

FIGS. 8A-8C are various drawings illustrating an example proximal expansion mechanism operable within any of the example embodiments. In this example, the proximal expansion mechanism includes a proximal wedge 8 with angled slots 81 that proximal endplate assembly pins 11 ride in (engage) to create the expansion forces upon translation of the proximal wedge 8. The proximal endplate assembly pins 11 extend through endplate guide slots 41 and into angled slots 81. The endplate guide slot 41 are vertical to guide expansion of the endplates caused by translation of the proximal wedge 8 with angled slots 81.

Figure 8D:
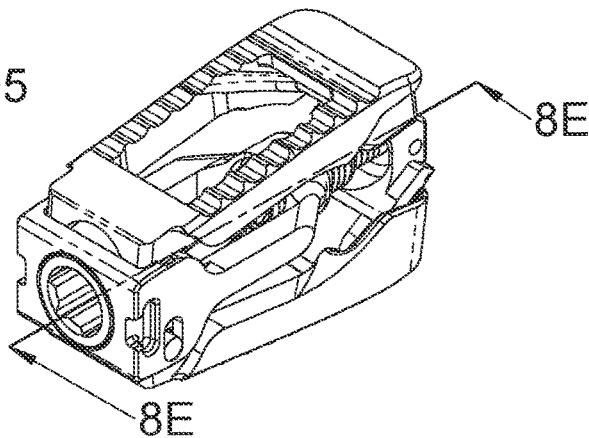
FIGS. 8D-8F are various drawings illustrating another example distal expansion mechanism operable within any of the example embodiments.
Figure 8E:
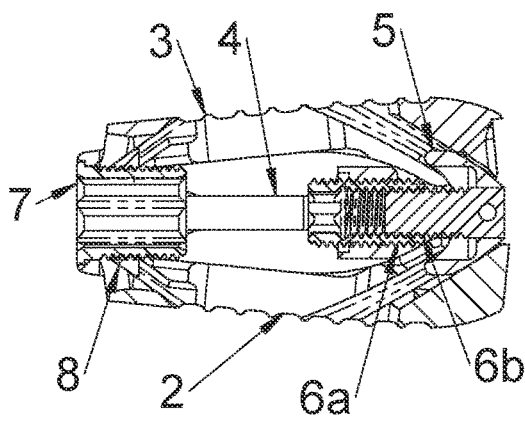
Figure 8F:
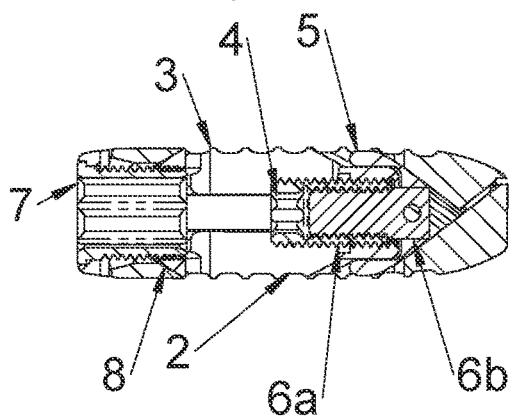
Figure 10A:
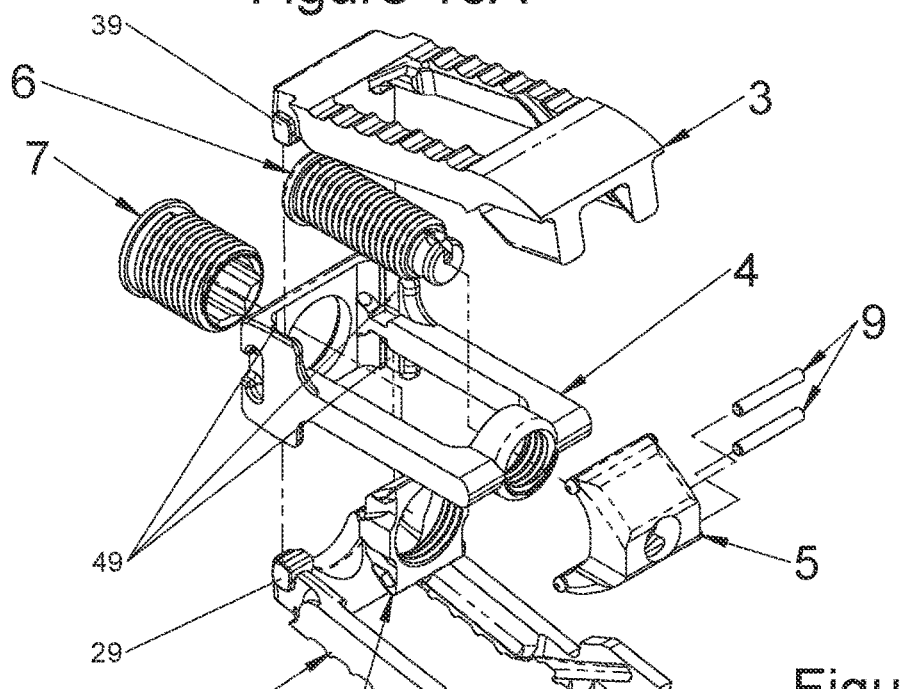
FIGS. 10A-10D are various drawings illustrating an example assembly technique for the expandable interbody implant according to various example embodiments.
Figure 10B:
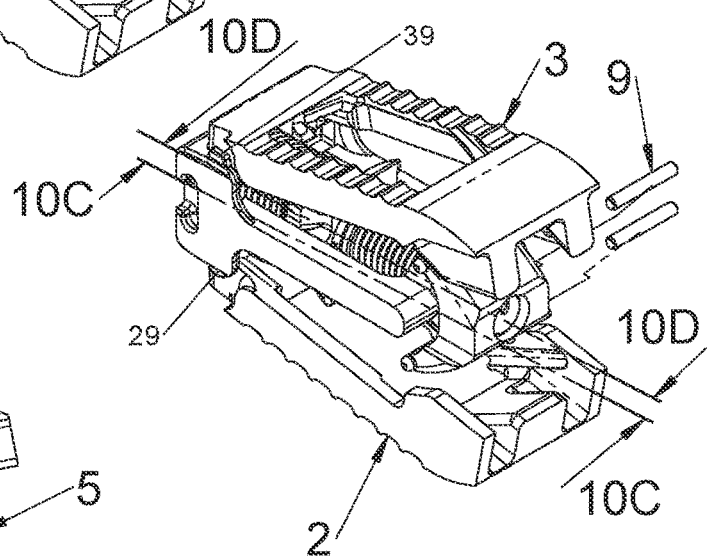
Figure 10C:
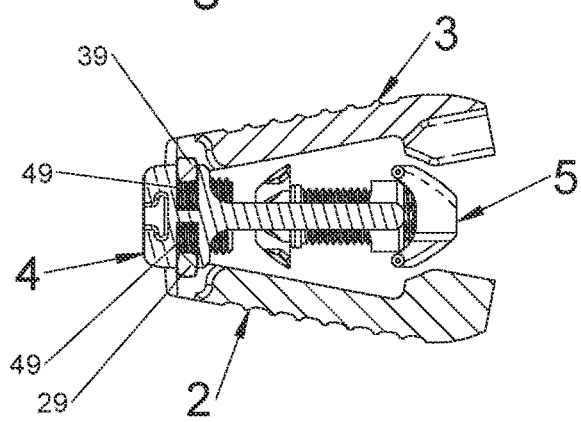
Figure 10D:
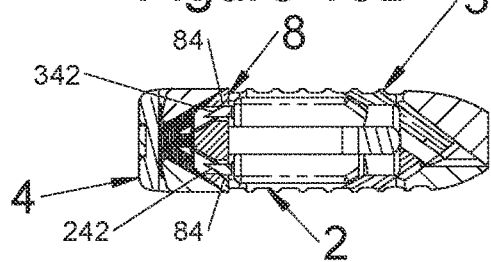
Figure 11A:
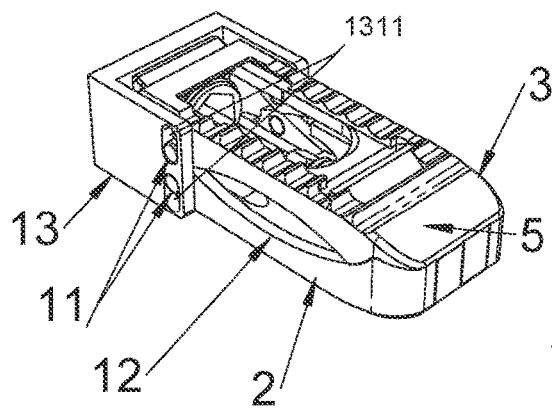
FIGS. 11A-11F are various drawings illustrating a proximal wedge integrated into a central frame according to an example embodiment.
Figure 11B:
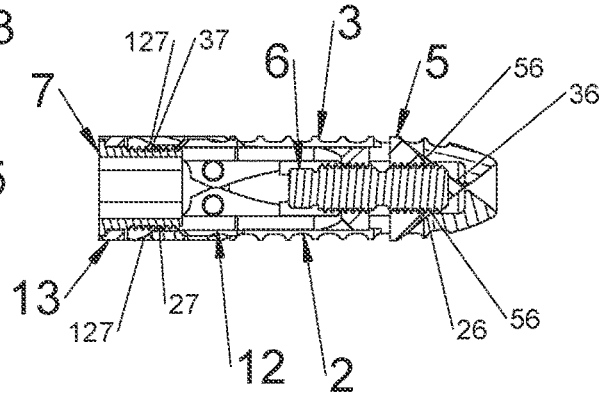
Figure 11C:
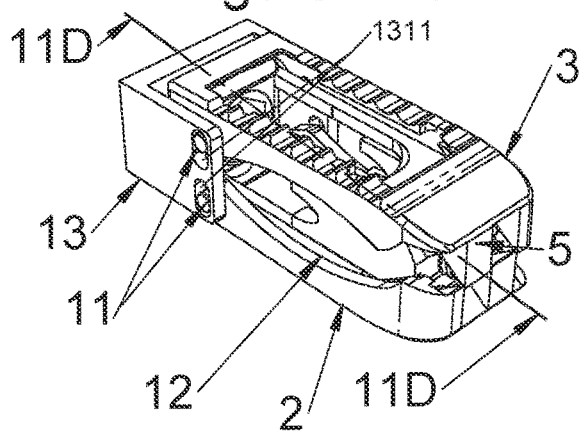
Figure 11D:
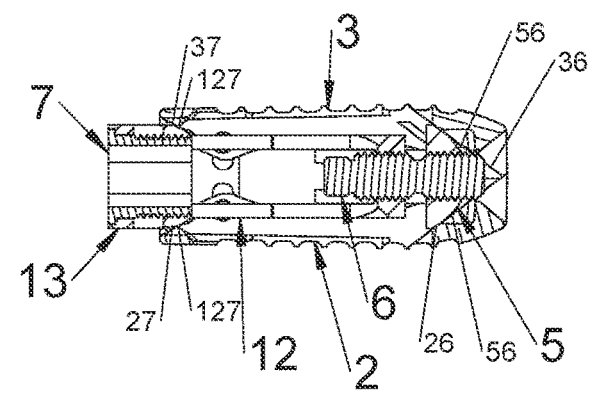
Figure 11E:
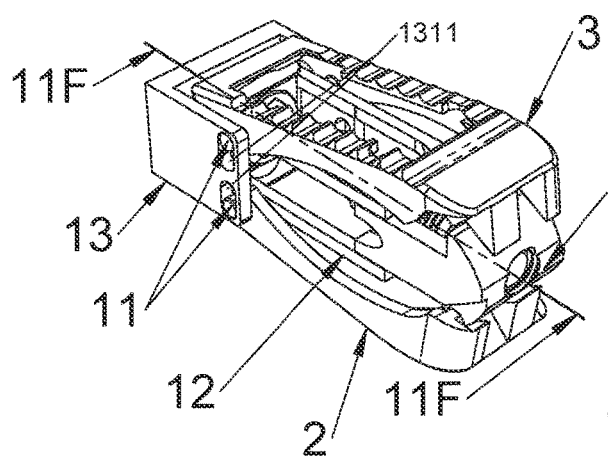
Figure 11F:
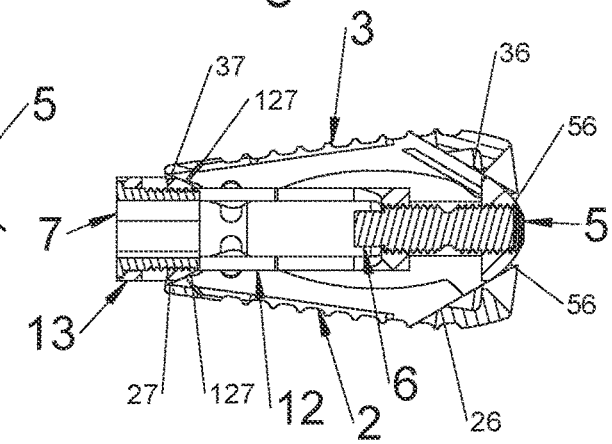

FIGS. 8D-8F are various drawings illustrating another example distal expansion mechanism operable within any of the example embodiments (also included in FIGS. 8A-8C). In this example, the distal expansion mechanism includes two threaded distal screws 6a, 6b. The inner distal screw 6b is secured to the distal wedge 5 on the distal end and threads into the outer distal screw 6a. The outer distal screw 6a includes an inner threaded bore to receive the inner distal screw 6a and outer threads that thread into a distal portion of the central frame 4. Upon rotation of the outer distal screw 6a, the outer distal screw translates due to interaction between the outer threaded surface and the central frame 4. Simultaneously, when the outer distal screw 6a rotates the inner distal screw 6b also translates with respect to the outer distal screw 6a causing expansion speed to double (over the standard single distal screw 6).

FIGS. 9A-9E are various drawings illustrating a double wedge distal expansion mechanism operative within any of the example embodiments. In this example, the distal expansion mechanism uses a dual wedge design, which are split into a lower distal wedge 5a and an upper distal wedge 5b. The dual wedges each include a vertical groove 581, 582 that cooperates with wedge retainer 682 to couple the wedges to distal screw 6. Rotation of distal screw 6 causes the lower wedge 5a and upper wedge 5b to advance distally and separate through interaction with structures on the central frame 4. The dual action of the split wedge design amplifies the amount of expansion achieved by the distal expansion mechanism.

FIGS. 9A-9E also illustrate a proximal expansion mechanism where the proximal wedge 8 bears against lateral faces of the endplates (lower endplate 2 and upper endplate 3) to create expansion between the endplates.

FIGS. 9F-9H are various drawings illustrating an example distal expansion mechanism operable within any of the example embodiments. In this example, the distal wedge 5 includes a extended frame portion 510 that translates within frame slot 415. The interaction of these structures (510/415) prevents any rotation of the distal wedge 5, but allows for translation of distal wedge 5 within the central frame 4.

FIGS. 10A-10D are various drawings illustrating an example assembly technique for the expandable interbody implant according to various example embodiments. In this example, the endplates, lower endplate 2 and upper endplate 3, can be inserted vertically into the central frame 4. The lower endplate pins 21 (not shown), 29 can slide directly into vertical guide grooves 49 from below, and similarly the upper endplate pins 31 (not shown), 39 can slide directly into vertical guides grooves 49 from above. The proximal screw 7 is inserted from the proximal end after the distal screw 6 is first inserted and threaded into the central frame 4. The distal screw 6 is captured by assembly pins 9 within the distal wedge 5.

FIGS. 11A-11F are various drawings illustrating a proximal wedge integrated into a central frame according to an example embodiment. In this example, the central frame 4 and the proximal wedge 8 are formed into a single structure (frame wedge 12). The frame wedge 12 includes angled surfaces 127 which interact with endplate angled surfaces 27, 37. Accordingly, in this example, actuation of the proximal screw 7 will advance both the frame wedge 12 (proximal wedge 8 integral with central frame 4) and the distal wedge 5. Actuation of the proximal screw 7 results in simultaneous expansion of both the proximal ends and distal ends of the lower endplate 2 and upper endplate 3. Expansion is parallel if the proximal wedge 8 and the distal wedge 5 as well as the corresponding ramped surfaces have the same inclination. In this example, the implant 1 also includes a separate distal screw 6 that can further advance the distal wedge 5. Actuation of the distal screw 6 results in inducing a lordotic angle to the expansion of implant 1. The endplates are retained in this example by a proximal outer fame 13, which forms the proximal end of implant 1 and wraps around a portion of the lateral sides. The endplates are retained by the proximal endplate assembly pins 11, which translate vertically within the endplate guide slots 1311.

Figure 12A:
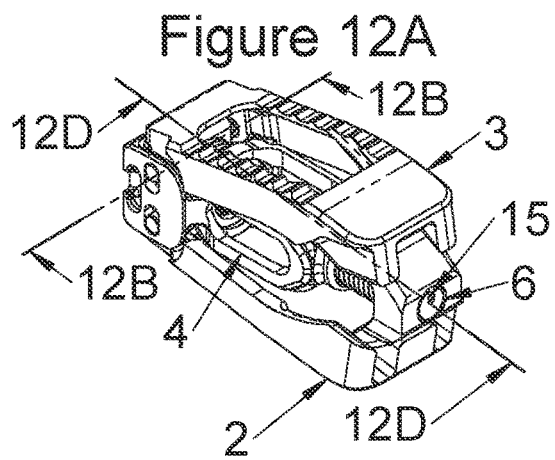
FIGS. 12A-12C are various drawings illustrating an elastic tab mechanism to limit rotation of a proximal screw, according to an example embodiment.
Figure 12B:
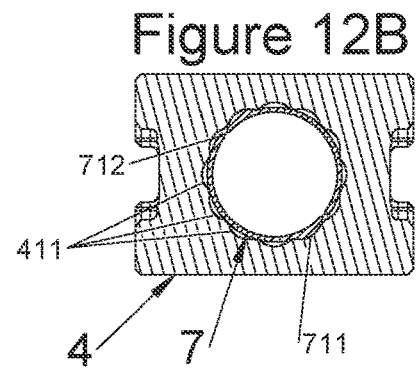
Figure 12D:
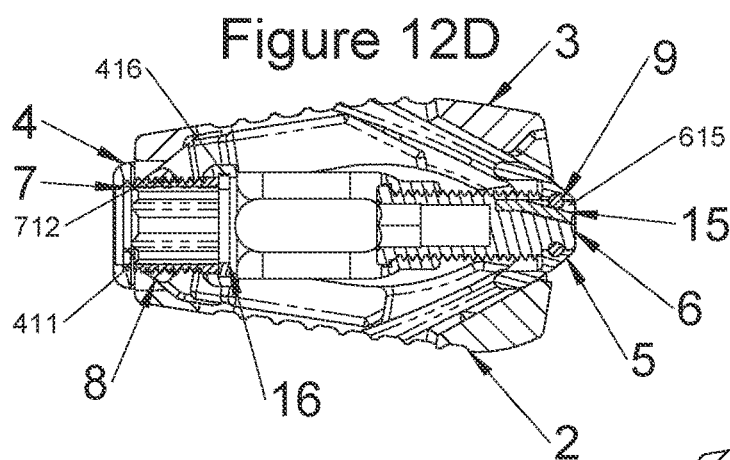
FIGS. 12D-12E are cross-sectional views illustrating uses of elastic pins to limit rotation of a proximal screw, according to various example embodiments.
Figure 12C:
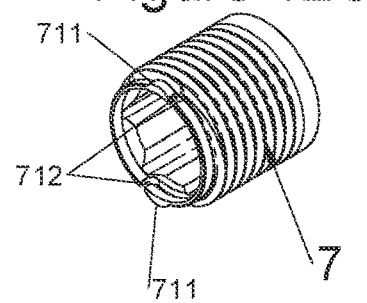

FIGS. 12A-12C are various drawings illustrating an elastic tab mechanism to limit rotation of the proximal screw 7, according to an example embodiment. In this example, the proximal screw 7 includes an elastic tab mechanism having opposing elastic locking tabs 711 and tab gaps 712. The elastic locking tabs 711 interact with locking recesses 411 formed in the bore receiving the proximal screw 7 within the central frame 4. The tab gaps 712 allow the elastic locking tabs 711 to flex, and snap into locking recesses 411 upon rotation of proximal screw 7.

Figure 12E:
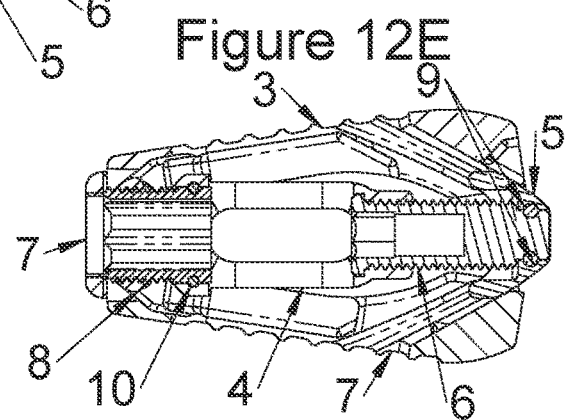

FIGS. 12D-12E are cross-sectional views illustrating uses of elastic pins to limit rotation of the proximal screw, according to various example embodiments. In this example, the elastic longitudinal pin 15 is inserted into the end of the distal screw 6 and interacts with pin housing 615 which allows for elastic flexion of elastic longitudinal pin 15 upon rotation of distal screw 6. The elastic longitudinal pin 15 interacts with assembly pins 9 to prevent unwanted rotation of distal screw 6, but allow rotation with the driver portion of the implant instrument.

This example also includes elastic ring 16, which assists in retaining the proximal screw 7 after assembly into the central frame 4. The elastic ring 16 maintains the proximal screw 7 in position after assembly.

Figure 12F:
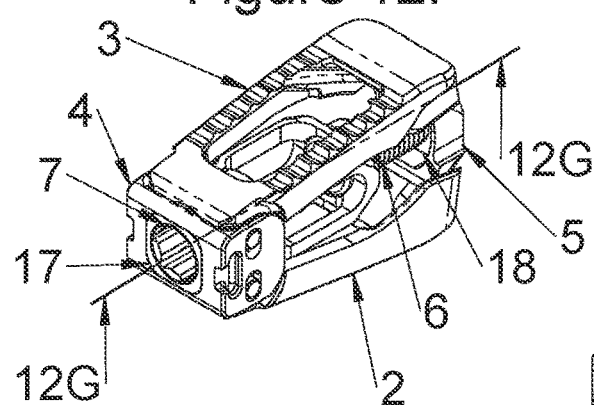
FIGS. 12F-12G are various drawings illustrating cylindrical polymer elements to limit rotation of a proximal screw, according to an example embodiment.
Figure 12G:
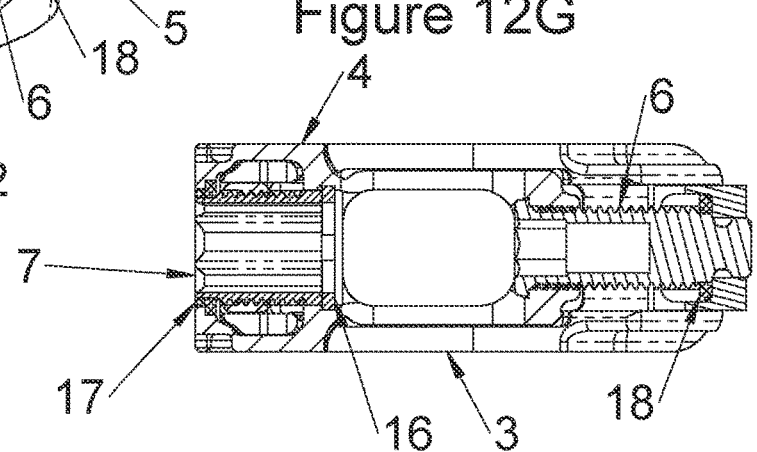

FIGS. 12F-12G are various drawings illustrating cylindrical polymer (PEEK) elements to limit rotation of a proximal screw, according to an example embodiment. The PEEK ring 17 is assembled with a light press fit on the proximal screw 7 and within a recess in the central frame 4. The PEEK ring 17 functions to avoid unintended rotation of the proximal screw 7 by friction. Similarly, the PEEK ring 18 is assembled with a light press fit on the distal screw 6 and within a recess in the distal wedge 5. The PEEK ring 18 also functions to avoid unintended rotation of the distal screw 6 by friction.

Interbody implant 1 of the present disclosure can be configured for use in various spinal correction procedures. Intervertebral implants of the present disclosure can be used with different insertion approaches and for various levels of the spine. Specifically, the illustrated example can be used as a Transforaminal Lumbar Interbody Fusion (TLIF) device or a Posterior Lumbar Interbody Fusion (PLIF) device. However, the features and benefits of the present disclosure can additionally be configured for use as an anatomic Anterior Cervical Interbody Fusion (ACIF) device or a lordotic Anterior Cervical Interbody Fusion (ACIF) device.

TLIF devices can be configured for insertion in between vertebrae from a posterior side of the spinal column. More specifically, a TLIF device of the present disclosure can be configured for insertion into a spinal column between a spinous process and an adjacent transverse process. A TLIF device of the present disclosure can be configured, e.g., with different thicknesses, sizes, widths, lengths to accommodate usage at different levels in the spinal column or in different sized patients. A TLIF device of the present application can be rotated on a superior-inferior axis in a transverse plane while being inserted to the position TLIF device to extend across the spinal column. An insertion device can be coupled to implant holder interface 45 can be pushed through tissue into the spinal column such that superior and inferior surfaces of the upper endplate 3 and lower endplate 2, respectively, align with an inferior surface of a superior vertebra and a superior surface of an inferior vertebra.

PLIF devices can be configured for insertion in between vertebrae from a posterior side of the spinal column. More specifically, a PLIF device of the present disclosure can be configured for insertion into a spinal column between a spinous process and an adjacent transverse process. A PLIF device of the present disclosure can be configured, e.g., with different thicknesses, sizes, widths, lengths to accommodate usage at different levels in the spinal column or in different sized patients. A PLIF device of the present disclosure can inserted straight into the spinal column on one side of the spinal cord. In examples, a second PLIF device can be inserted straight into the spinal column on the opposite side of the spinal column. An insertion device can be coupled to implant holder interface 45 can be pushed through tissue into the spinal column such that superior and inferior surfaces the upper endplate 3 and lower endplate 2, respectively, align with an inferior surface of a superior vertebra and a superior surface of an inferior vertebra.

The systems, devices and methods discussed in the present application can be useful in implanting expandable interbody implants, such as those that can be used in spinal correction procedures involving lateral, transverse, anterior or posterior insertion of a spacer between adjacent vertebrae. The interbody implant can have first and second bodies that can be coupled to each other at a pivoting coupling. The angle between the lower endplate 2 and the upper endplate 3 can be adjusted to push adjacent anatomy into a desired orientation, such as a desired angle therebetween. The lower endplate 2 and the upper endplate 3 can be moved into the desired angle using two expansion mechanisms that can provide different actuation qualities, such as expansion strength or force, expansion height and mechanical leverage. Thus, the two expansion mechanisms can be arranged in conjunction with an actuation mechanism to sequentially operate to pivot the lower endplate 2 and the upper endplate 3 relative to each other to overcome resistance from the anatomy and position the anatomy in the desired orientation. The first expansion mechanism can be configured to adjust a distal portion of the implant. The second expansion mechanism can be configured to adjust a proximal portion of the implant to create a desire lordotic correction.

EXAMPLES

Each of the following non-limiting examples may stand on its own, or may be combined in various permutations or combinations with one or more of the other examples. Structures of the discussed expandable implants may be utilized across multiple different examples, even where not specifically discussed in a particular combination. For example, different example embodiments discussed above in view of the figures include different wedge structures for expanding end plates, the different wedge structures can be adapted for use with different end plate structures as would be understood by one of ordinary skill in the art.

Example 1 is an expandable interbody implant including a central frame, a superior end plate, an inferior end plate, an anterior adjustment mechanism and a posterior adjustment mechanism. In the broadest understanding of this example, the expandable interbody implant includes the two independently adjustable adjustment mechanisms (e.g., anterior and posterior) that operate to separate the superior and inferior end plates. In this example, the central frame includes an anterior (distal) threaded bore and a posterior (proximal) bore. The superior (upper) end plate is movably coupled along a posterior portion of the central frame. The inferior (lower) end plate is movably coupled along the posterior portion of the central frame opposite the superior end plate. The anterior adjustment mechanism includes an anterior wedge coupled to an anterior screw movable within the anterior threaded bore. While the posterior adjustment mechanism includes a posterior wedge coupled to a posterior screw movable within the posterior bore.

In Example 2, the subject matter of Example 1 can optionally include the anterior adjustment mechanism being adapted to adjust an anterior superior-inferior separation between the superior end plate and the inferior end plate.

In Example 3, the subject matter of any one of Examples 1 or 2 can optionally include the posterior adjustment mechanism being adapted to adjust a posterior superior-inferior separation between the superior end plate and the inferior end plate.

In Example 4, the subject matter of any one of Examples 1 to 3 can optionally include the anterior adjustment mechanism operating independently of the posterior adjustment mechanism.

In Example 5, the subject matter of any one of Examples 1 to 4 can optionally include the anterior wedge engaging corresponding anterior ramped surfaces extending from an inferior side of an anterior portion of the superior end plate.

In Example 6, the subject matter of any one of Examples 1 to 5 can optionally include the posterior wedge engaging corresponding posterior ramped surfaces extending from an inferior side of a posterior portion of the superior end plate.

In Example 7, the subject matter of any one of Examples 1 to 4 can optionally include the superior end plate including a pair of anterior ramped surfaces extending inferiorly, and the inferior end plate includes a central anterior ramped surface extending superiorly.

In Example 8, the subject matter of Example 7 can optionally include the expandable interbody implant in a collapsed state, the pair of anterior ramped surfaces extending from the superior end plate are received within recesses on either side of the central anterior ramped surface of the inferior end plate.

In Example 9, the subject matter of any one of Examples 1 to 8 can optionally include the anterior wedge including over expansion stops extending laterally from outer edges.

In Example 10, the subject matter of Example 9 can optionally include the over expansion stops being received within grooves within lateral walls of the superior end plate and the inferior end plate.

In Example 11, the subject matter of any one of Examples 1 to 10 can optionally include the anterior screw being rotationally coupled to the anterior wedge.

In Example 12, the subject matter of Example 11 can optionally include rotation of the anterior screw advancing the anterior screw within the threaded anterior bore resulting in linear advancement of the anterior wedge against anterior ramped surfaces of the superior end plate and inferior end plate.

In Example 13, the subject matter of any one of Examples 1 to 10 can optionally include the anterior screw including a first threaded section and a second threaded section.

In Example 14, the subject matter of Example 13 can optionally include the first threaded section engaging the anterior threaded bore and the second threaded section engaging a second threaded bore within the anterior wedge.

In Example 15, the subject matter of Example 14 can optionally include the first threaded section including a first thread pitch oriented in a first direction and the second threaded section including a second thread pitch oriented in a second direction, wherein the first direction is opposite the second direction.

In Example 16, the subject matter of Example 15 can optionally include the central frame including a guiding structure to prevent rotation of the anterior wedge upon rotation of the anterior screw.

In Example 17, the subject matter of any one of Examples 1 to 10 can optionally include the posterior screw being translationally fixed relative to the central frame and free to rotate within the posterior bore.

In Example 18, the subject matter of Example 17 can optionally include the posterior wedge including a second threaded bore receiving a portion of the posterior screw, and upon rotation of the posterior screw the posterior wedge translates linearly with respect to the central frame.

In Example 19, the subject matter of any one of claims 1 to 10 can optionally include the posterior bore being threaded, and the posterior screw being threadably coupled within the posterior bore to enable rotation and translation of the posterior screw with respect to the central frame.

In Example 20, the subject matter of Example 19 can optionally include the posterior screw being rotationally coupled to the posterior wedge, and the posterior wedge translates with the posterior screw with respect to the central frame.

In Example 21, the subject matter of any one of Examples 1 to 20 can optionally include the posterior screw being captured within the posterior bore by an elastic tab engaging a groove within the posterior bore.

In Example 22, the subject matter of any one of Examples 1 to 20 can optionally include the posterior screw being captured within the posterior bore by an offset elastic pins perpendicular to a longitudinal screw axis.

In Example 23, the subject matter of any one of Examples 1 to 20 can optionally include rotation of the anterior screw being limited by an elastic pin positioned parallel and offset to a longitudinal axis of the anterior screw.

VARIOUS NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An expandable interbody implant comprising:
   a central frame including an anterior threaded bore and a posterior bore;
   a superior end plate movably coupled along a posterior portion of the central frame;
   an inferior end plate movably coupled along the posterior portion of the central frame opposite the superior end plate;
   an anterior adjustment mechanism including an anterior wedge coupled to an anterior screw movable within the anterior threaded bore; and
   a posterior adjustment mechanism including a posterior wedge coupled to a posterior screw movable within the posterior bore,
   wherein at least a portion of the central frame is positioned between the superior end plate and the inferior end plate when the expandable interbody implant is in a collapsed position.

2. The expandable interbody implant of claim 1, wherein the anterior adjustment mechanism is adapted to adjust an anterior superior-inferior separation between the superior end plate and the inferior end plate.

3. The expandable interbody implant of claim 2, wherein the posterior adjustment mechanism is adapted to adjust a posterior superior-inferior separation between the superior end plate and the inferior end plate.

4. The expandable interbody implant of claim 3, wherein the anterior adjustment mechanism operates independently of the posterior adjustment mechanism.

5. The expandable interbody implant of claim 1, wherein the anterior wedge engages corresponding anterior ramped surfaces extending from an inferior side of an anterior portion of the superior end plate.

6. The expandable interbody implant of claim 1, wherein the posterior wedge engages corresponding posterior ramped surfaces extending from an inferior side of a posterior portion of the superior end plate.

7. The expandable interbody implant of claim 1, wherein the superior end plate includes a pair of anterior ramped surfaces extending inferiorly, and the inferior end plate includes a central anterior ramped surface extending superiorly.

8. The expandable interbody implant of claim 7, wherein with the expandable interbody implant in the collapsed position, the pair of anterior ramped surfaces extending inferiorly from the superior end plate are received within recesses on either side of the central anterior ramped surface of the inferior end plate.

9. The expandable interbody implant of claim 1, wherein the anterior wedge includes over expansion stops extending laterally from outer edges thereof, and wherein the over expansion stops are received within grooves within lateral walls of the superior end plate and the inferior end plate.

10. The expandable interbody implant of claim 1, wherein the anterior screw is rotationally coupled to the anterior wedge.

11. The expandable interbody implant of claim 10, wherein rotation of the anterior screw advances the anterior screw within the anterior threaded bore resulting in linear advancement of the anterior wedge against anterior ramped surfaces of the superior end plate and inferior end plate.

12. The expandable interbody implant of claim 1, wherein the anterior screw includes a first threaded section and a second threaded section.

13. The expandable interbody implant of claim 12, wherein the first threaded section engages the anterior threaded bore and the second threaded section engages a second threaded bore within the anterior wedge.

14. The expandable interbody implant of claim 13, wherein the first threaded section includes a first thread pitch oriented in a first direction and the second threaded section includes a second thread pitch oriented in a second direction, wherein the first direction is opposite the second direction.

15. The expandable interbody implant of claim 14, wherein the central frame includes a guiding structure to prevent rotation of the anterior wedge upon rotation of the anterior screw.

16. The expandable interbody implant of claim 1, wherein the posterior screw is translationally fixed relative to the central frame and free to rotate within the posterior bore.

17. The expandable interbody implant of claim 16, wherein the posterior wedge includes a second threaded bore receiving a portion of the posterior screw, and upon rotation of the posterior screw the posterior wedge translates linearly with respect to the central frame.

18. The expandable interbody implant of claim 1, wherein the posterior bore is threaded, and the posterior screw is threadably coupled within the posterior bore to enable rotation and translation of the posterior screw with respect to the central frame, wherein the posterior screw is rotationally coupled to the posterior wedge, and the posterior wedge translates with the posterior screw with respect to the central frame.

19. An expandable interbody implant comprising:
   a central frame including an anterior threaded bore and a posterior bore;
   a superior end plate movably coupled along a posterior portion of the central frame;
   an inferior end plate movably coupled along the posterior portion of the central frame opposite the superior end plate;
   an anterior adjustment mechanism including an anterior wedge coupled to an anterior screw movable within the anterior threaded bore; and
   a posterior adjustment mechanism including a posterior wedge coupled to a posterior screw movable within the posterior bore,
   wherein the superior end plate includes a pair of anterior ramped surfaces extending inferiorly, and the inferior end plate includes a central anterior ramped surface extending superiorly,
   wherein with the expandable interbody implant in a collapsed state, the pair of anterior ramped surfaces extending inferiorly from the superior end plate are received within recesses on either side of the central anterior ramped surface of the inferior end plate.

20. An expandable interbody implant comprising:
   a central frame including an anterior threaded bore and a posterior bore;
   a superior end plate movably coupled along a posterior portion of the central frame;
   an inferior end plate movably coupled along the posterior portion of the central frame opposite the superior end plate;
   an anterior adjustment mechanism including an anterior wedge coupled to an anterior screw movable within the anterior threaded bore; and
   a posterior adjustment mechanism including a posterior wedge coupled to a posterior screw movable within the posterior bore,
   wherein the posterior bore is threaded, and the posterior screw is threadably coupled within the posterior bore to enable rotation and translation of the posterior screw with respect to the central frame, and wherein the posterior screw is rotationally coupled to the posterior wedge, and the posterior wedge translates with the posterior screw with respect to the central frame.

* * * * *